US009465024B2

(12) United States Patent
Kevil et al.

(10) Patent No.: US 9,465,024 B2
(45) Date of Patent: Oct. 11, 2016

(54) MEASUREMENT OF BIOLOGICALLY LABILE HYDROGEN SULFIDE POOLS

(71) Applicant: Board of Supervisors of Louisiana State University and Agricultural and Mechanical College, Baton Rouge, LA (US)

(72) Inventors: Christopher G. Kevil, Shreveport, LA (US); Xinggui Shen, Shreveport, LA (US); Elvis A. Peter, Kronenwetter, WI (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 117 days.

(21) Appl. No.: 14/387,999

(22) PCT Filed: Mar. 14, 2013

(86) PCT No.: PCT/US2013/031354
§ 371 (c)(1),
(2) Date: Sep. 25, 2014

(87) PCT Pub. No.: WO2013/148246
PCT Pub. Date: Oct. 3, 2013

(65) Prior Publication Data
US 2015/0056713 A1    Feb. 26, 2015

Related U.S. Application Data

(60) Provisional application No. 61/617,995, filed on Mar. 30, 2012.

(51) Int. Cl.
*G01N 33/84* (2006.01)
*G01N 33/50* (2006.01)
(Continued)

(52) U.S. Cl.
CPC .............. *G01N 33/50* (2013.01); *G01N 33/84* (2013.01); *G01N 21/64* (2013.01); *G01N 2021/7786* (2013.01); *Y10T 436/184* (2015.01)

(58) Field of Classification Search
CPC ...... G01N 33/84; G01N 33/50; G01N 21/64; G01N 2021/7786
USPC .................................. 436/119–121, 123, 172
See application file for complete search history.

(56) References Cited

U.S. PATENT DOCUMENTS 6,340,596 B1 * 1/2002 Sugiyama .............. G01N 31/22
                                                    436/119
6,468,762 B1   10/2002 Tan ...................................... 5/24
(Continued)

OTHER PUBLICATIONS

Rethmeier, J. et al, Journal of Chromtography A 1997, 760, 295-302.*
(Continued)

*Primary Examiner* — Arlen Soderquist
(74) *Attorney, Agent, or Firm* — Davis and Bujold PLLC

(57) ABSTRACT

A method to measure all relevant biologic hydrogen sulfide pools, namely free hydrogen sulfide, acid-labile sulfide, and bound sulfane sulfur, has been developed. This new method involves selective liberation, trapping and derivatization of labile hydrogen sulfide. The total labile sulfide, including the contribution of the bound sulfane sulfur pool, the acid-labile pool, and free H2S, was measured by incubating the sample with a reducing agent, TCEP (Tris(2-carboxyethyl)phosphine hydrochloride), to reduce disulfide bonds in an acid solution. This method was used to measure the three sulfide pools in blood samples from mice and from humans. This method can be used for research, environmental, and clinical diagnostic purposes in determining hydrogen sulfide bioavailability in biological or other samples.

19 Claims, 10 Drawing Sheets

(51) Int. Cl.
    *G01N 21/64* (2006.01)
    *G01N 21/77* (2006.01)

(56) References Cited

U.S. PATENT DOCUMENTS

2007/0078113 A1 4/2007 Roth et al. ............... 514/114
2008/0164156 A1 7/2008 Zhang et al. ............. 205/778
2012/0073988 A1 3/2012 Zhang et al. ........... 205/786.5

OTHER PUBLICATIONS

Tangerman, A., Journal of Chromatography B 2009, 877, 3366-3377.*
Franz,B. et al, Microbiology 2009, 155, 2766-2774.*
Dombkowski, R. A. et al., "Hydrogen sulfide as an endogenous regulator of vascular smooth muscle tone in trout," American journal of physiology, vol. 286, No. 4, pp. R678-685 (2004).
Graham, D. E. et al., "Reductive dehalogenation of monobromobimane by tris(2-carboxyethyl)phosphine," Analytical biochemistry, vol. 318, pp. 325-328 (2003).
Gru, Cécile et al., "Determination of Reduced Sulfur Compounds by High-Performance Liquid Chromatography n Hydrothermal Seawater and Body Fluids from *Riftia pachyptila*," Analyst, vol. 123, pp. 1289-1293 (1998).
Hughes, M. N. et al., "Making and working with hydrogen sulfide: The chemistry and generation of hydrogen sulfide in vitro and its measurement in vivo: a review," Free radical biology & medicine, vol. 47, pp. 1346-1353 (2009).
Ishigami, M. et al., "A source of hydrogen sulfide and a mechanism of its release in the brain," Antioxidants & redox signaling, vol. 11, pp. 205-214 (2009).
Johnson, Deborah C. et al., "Structure, function, and formation of biological iron-sulfur clusters," Annual review of biochemistry, vol. 74, pp. 247-281 (2005).
Kabil, Omer et al., "Redox biochemistry of hydrogen sulfide," Journal of biological chemistry, vol. 285, No. 29, pp. 21903-21907 (2010).
Kajimura, Mayumi et al., "Interactions of multiple gas-transducing systems: hallmarks and uncertainties of CO, NO, and H2S gas biology," Antioxidants & redox signaling, vol. 13, No. 2, pp. 157-192 (2010).
Kolluru, G.K. et al., "Detection of hydrogen sulfide in biological samples: current and future," Expert Reviews, vol. 4, pp. 9-12 (2011).
Kosower, N. S. et al., "Thiol labeling with bromobimanes," Methods in enzymology, vol. 143, pp. 76-84 (1987).
Levu, M. et al., "Hydrogen sulfide-mediated cardioprotection: mechanisms and therapeutic potential," Clin Sci (Lond), vol. 120, pp. 219-229; 2011.
Levitt, M. D. et al., "Free and acid-labile hydrogen sulfide concentrations in mouse tissues: anomalously high free hydrogen sulfide in aortic tissue," Antioxidants & redox signaling, vol. 15, pp. 373-378 (2011).
Lippert, A. R. et al., "Reaction-based fluorescent probes for selective imaging of hydrogen sulfide in living cells," Journal of the American Chemical Society, vol. 133, pp. 10078-10080 (2011).
Liu, Yi-Hong et al., "Hydrogen Sulfide in the Mammalian Cardiovascular System," Antioxidants & Redox Signaling, vol. 17, No. 1, pp. 141-185 (2012).
Mathai, J. C. et al., "No facilitator required for membrane transport of hydrogen sulfide," Proceedings of the National Academy of Sciences of the United States of America, vol. 106, pp. 16633-16638 (2009).
Mubeen, S. et al., "Sensitive detection of H2S using gold nanoparticle decorated single-walled carbon nanotubes," Analytical chemistry, vol. 82, pp. 250-257 (2010).
O'Reilly, J.W. et al., "Chromatographic and electrophoretic separation of inorganic sulfur and sulfur-oxygen species," Analytica Chimica Acta, vol. 432, pp. 165-192 (2001).
Olson, K. R., "The therapeutic potential of hydrogen sulfide: separating hype from hope," American journal of physiology, vol. 301, pp. R297-312 (2011).
Olson, K. R., "Is hydrogen sulfide a circulating 'gasotransmitter' in vertebrate blood?" Biochimica et biophysica acta, vol. 1787, pp. 856-863 (2009).
Olson, K.H., "A practical look at the chemistry and biology of hydrogen sulfide," Antioxidants & Redox Signaling, vol. 17, pp. 32-44 (2012).
Peng, H. et al., "A Fluorescent Chemoprobe for Fast and Quantitative Detection of Hydrogen Sulfide in Blood," Angewandte Chem. Int'l ed. Engl, vol. 50, No. 41, pp. 9672-9675 (2011).
Qian, Y. et al., "Selective fluorescent probes for live-cell monitoring of sulphide," Nature communications, vol. 2, pp. 495 (2011).
Shen, X. et al., "Analytical Measurement of Discrete Hydrogen Sulfide Pools in Biological Specimens," Free Radical Biology & Medicine, vol. 52, pp. 2276-2283 (2012).
Shen, X. et al., "Measurement of plasma hydrogen sulfide in vivo and in vitro," Free radical biology & medicine, vol. 50, pp. 1021-1031 (2011).
Togawa, T. et al., "High performance liquid chromatographic determination of bound sulfide and sulfite and thiosulfate at their low levels in human serum by pre-column fluorescence derivatization with monobromobimane," Chemical & Pharmaceutical Bulletin, vol. 40, pp. 3000-3004 (1992).
Tyagarajan, K. et al., "Thiol-reactive dyes for fluorescence labeling of proteomic samples," Electrophoresis, vol. 24, pp. 2348-2358 (2003).
Ubuka, T., "Assay methods and biological roles of labile sulfur in animal tissues," J. Chromatogr. B Anal. Technol. Biomed. Life Sci., vol. 781, pp. 227-249 (2002).
Wang, R., "Two's company, three's a crowd: can H2S be the third endogenous gaseous transmitter?" The FASEB journal : official publication of the Federation of American Societies for Experimental Biology, vol. 16, pp. 1792-1798 (2002).
Whiteman, M. et al., "Emerging role of hydrogen sulfide in health and disease: critical appraisal of biomarkers and pharmacological tools," Clin Sci (Lond), vol. 121, pp. 459-488 (2011).
Wintner, E. A. et al., "A monobromobimane-based assay to measure the pharmacokinetic profile of reactive sulphide species in blood," British journal of pharmacology, vol. 160, pp. 941-957 (2010).
Zhang, B. H. et al., "Fluorescent method for the determination of sulfide anion with ZnS:Mn quantum dots," Journal of fluorescence, vol. 20, pp. 243-250 (2010).
Zhao, W. et al., "The vasorelaxant effect of H(2)S as a novel endogenous gaseous $K_{ATP}$ channel opener," The EMBO journal, vol. 20, pp. 6008-6016 (2001).

* cited by examiner

MEASUREMENT OF BIOLOGICALLY LABILE HYDROGEN SULFIDE POOLS

This is the United States national stage of international application PCT/US2013/031354, international filing date Mar. 14, 2013, which claims the benefit of the Mar. 30, 2012 filing date of U.S. provisional patent application Ser. No. 61/617,995 under 35 U.S.C. §119(e).

TECHNICAL FIELD

This invention pertains to an analytical method for measuring total labile hydrogen sulfide in bioavailable pools, and to a method to measure each of the three discrete bioavailable pools of hydrogen sulfide from clinical and research samples, including, but not limited to, blood, tissues, fluids, and environmental samples.

BACKGROUND ART

Hydrogen sulfide ($H_2S$) is a ubiquitous gaseous signaling molecule that plays a vital role in numerous cellular functions [1-5]. It has also become the focus of many research endeavors, including pharmaco-therapeutic manipulation [1-5]. One of the challenges facing the field is the accurate measurement of biologically active $H_2S$. The complexity of analytical $H_2S$ measurement, especially in living organisms, reflects the fact that hydrogen sulfide is a volatile gas and exists in the organism in different forms, including a free form ("free $H_2S$"), an acid labile pool, and as bound sulfane sulfur, as shown in FIG. 1.

Sulfur exists in the body in several forms, ranging from a fully reduced divalent state as sulfide to a fully oxidized hexavalent state as sulfate [1, 9, 10]. Measurement of biologic sulfur has focused on measuring sulfide (the reduced divalent state), in part because of difficulties in accurately measuring other states. Sulfur equivalents in the reduced divalent state are very reactive within biological matrices, resulting in sulfide equivalents being present in three different volatile sulfur pools, as shown in FIG. 1. All three pools are important in regulating the amount of bioavailable sulfur with the most important being the acid labile and bound sulfane sulfur pools [10, 11].

Hydrogen sulfide is produced predominantly enzymatically from cysteine, for example, using two pyridoxal-5'-phosphate dependent enzymes, cystathionine-β-synthase and cystathionine-γ-lyase, as well as 3-mercaptosulfurtransferase. Free hydrogen sulfide can diffuse across cellular membranes without the need for a specialized transporter [4, 6]. Free $H_2S$ is found dissolved in plasma and other tissue fluids. At mammalian body conditions, i.e., pH 7.4 and temperature of 37° C., 18.5% of free hydrogen sulfide exists as $H_2S$ gas, and the remainder is almost all hydrosulfide anion (HS—) with a negligible contribution of $S^{2-}$ [7, 8].

Sulfane sulfur refers to divalent sulfur atoms bound to another sulfur, though they may bear an ionizable hydrogen at some pH values. Examples of these bound sulfurs include thiosulfate $S_2O_3^{2-}$, persulfides R—S—SH, thiosulfonates R—S(O)—S—R', polysulfides R—$S_n$—R, polythionates $S_nO_6^{2-}$, and elemental sulfur $S^0$ [10]. These sulfane-bound sulfurs can be released under reducing conditions. Acid labile sulfide, the other major bioavailable pool, consists of sulfur present in iron-sulfur clusters contained in iron-sulfur proteins (non-heme), which are ubiquitous in living organisms, and include a variety of proteins and enzymes, including without limitation, rubredoxins, ferredoxins, aconitase, and succinate dehydrogenase [10, 12]. The acid labile sulfides readily liberate free $H_2S$ in acid conditions (pH<5.4). The process of acid liberation may also release hydrogen sulfide from persulfides, which have traditionally been classified as sulfane sulfur [13]. This "acid labile sulfide pool" has been postulated to be a "reversible sulfide sink" and may be an important storage pool that regulates the amount of bioavailable free hydrogen sulfide [14]. However, the bound sulfur forms may be more important in storing and release of exogenously administered sulfide [11].

A weakness to the study of sulfide has been the lack of precise methodology for the accurate and reproducible measurement of hydrogen sulfide both in vivo and in vitro. A variety of methods to measure free $H_2S$ have been employed with divergent results [10, 13, 15]. These methods include a spectrophotometric derivatization method resulting in methylene blue formation, variations of this methylene blue method using high performance liquid chromatography [10], sulfide ion-selective electrodes, polarographic sensors [16], gas chromatography [13, 17], and HPLC in conjunction with fluorimetric based methods using monobromobimane (MBB) to derivatize free $H_2S$ [14, 18, 39, 41].

The levels of $H_2S$ in a mammalian body that have been measured range from nanomolar to hundreds of micromolar concentrations [10, 15]. This wide range is partially due to the various methods of measuring the $H_2S$. The previously favored methylene blue method of hydrogen sulfide detection had several disadvantages: the method had interference from bound sulfide pools, was subject to chemical artifacts, and was unable to actual free hydrogen sulfide. Moreover, methylene blue readily forms dimer and trimer aggregates in aqueous media that does not conform to Beer's law which further prevents accurate analytical measurement of bio available sulfide [18].

Earlier attempts to characterize the bound sulfane sulfur pool have primarily utilized MBB in conjunction with dithiothreitol (DTT) as a reducing agent to free the bound sulfide [10, 21]. Most work has focused on the free hydrogen sulfide and acid labile pools alone [11, 13]. These study results were limited because of various problematic issues such as pH, volatilization, and oxidation of the measured samples [40].

The fluorescent reagent MBB has been widely used to measure various thiol-containing species through alkylation [22]. S-alkylation occurs twice with sulfide under alkaline conditions, forming sulfide-dibimane. We have previously reported a fluorimetric, reverse-phase (RP)-HPLC analytical method that stabilizes biologically active free hydrogen sulfide from oxidation while able to detect low levels. This analytical method measured free plasma hydrogen sulfide by derivatization of sulfide with an excess of MBB under alkaline, low oxygen, and trace metal-free conditions with RP-HPLC separation and fluorescent detection of the fluorescent sulfide-dibimane product with a detection level of about 2 nM [18].

The field of hydrogen sulfide measurement continues to evolve with modifications of various methods, including the report of different fluorescent probes [33-35] as well as applications of new technologies, such as nanotubes and quantum dots [36, 37], and a method for measurement of hydrogen sulfide dissolved in aqueous solutions through the use of an electrochemical sensor [38]. However, there is no reported method for accurately measuring all labile hydrogen sulfide pools to determine hydrogen sulfide bioavailability in biological or other samples that contain biologically derived tissues or proteins, e.g., environmental water samples. There is a need for a method that allows for an accurate, quantitative, and scalable measurement of discrete pools of hydrogen sulfide from primary labile sulfide pools to use in both experimental and clinical samples.

U.S. Pat. No. 6,468,762 discloses a method to measure homocysteine using N,N-dipropyl-phenylene diamine and using dithiothreitol as a reducing agent.

U.S. Patent Application Publication No. 2007/0078113 discloses a method to measure hydrogen sulfide in blood using an extractive alkylation technique coupled with gas chromatography and mass specific detection to quantify hydrogen sulfide, and using a denaturing/reducing reaction buffer of benzalkonium chloride, tetraethylammonium hydroxide, and tris(2-carboxyethyl)phosphine hydrochloride in saturated borate buffer.

U.S. Patent Application Publication No. 2012/0073988 discloses an electrochemical sensor to measure hydrogen sulfide.

DISCLOSURE OF THE INVENTION

We have discovered a method to measure all relevant biologic hydrogen sulfide pools, namely free hydrogen sulfide, acid-labile sulfide, and bound sulfane sulfur. We have developed a new protocol to discretely measure specific labile $H_2S$ pools using the monobromobimane (MBB) method coupled with RP-HPLC. This new protocol involves selective liberation, trapping and derivatization of labile $H_2S$. The free $H_2S$ was measured using our earlier method employing excess MBB under alkaline, 1% oxygen, and trace-metal-free conditions followed by RP-HPLC and fluorescence detection of the sulfide dibimane product. Acid-labile $H_2S$ was released by incubating the sample in an acidic solution (e.g., pH 2.6, 100 mM phosphate buffer with 0.1 mM DTPA) and measured along with free $H_2S$ in an enclosed system to contain the volatilized $H_2S$. Volatilized and free $H_2S$ was then trapped in an alkaline solution (e.g., 100 mM Tris-HCl, pH 9.5, 0.1 mM DTPA), and then reacted with excess monobromobimane to form the stable fluorimetric product sulfide-dibimane. In a separate sample aliquot, the total labile sulfide, including the contribution of bound sulfane sulfur pool, the acid-labile pool, and free $H_2S$, was measured by incubating the sample with the reducing agent TCEP (Tris(2-carboxyethyl)phosphine hydrochloride), to reduce disulfide bonds in an acid solution (e.g., in 100 mM phosphate buffer, pH 2.6, 0.1 mM DTPA), and after removing the solution, the volatilized $H_2S$ was trapped using alkaline buffer with MBB as described above.

The amount of sulfide in the three individual sulfide pools was then determined by the following. The amount of free $H_2S$ is directly measured. The amount of acid-labile sulfide is the difference between the measurement of acid-labile+ free $H_2S$ and the measurement of free $H_2S$. Finally, the amount of bound sulfane sulfur is the difference in the measurement of total sulfide and the measurement of acid-labile+free $H_2S$. This new method allows a very sensitive and accurate measurement of the three primary biological pools of $H_2S$ including free, acid labile, and bound sulfane sulfur in various biological specimens. We have used this method to measure the sulfide pools in blood samples from both mice and humans. We have also optimized the method to produce a more accurate measurement of all three pools. This new method can be used for research, environmental, and clinical diagnostic purposes in determining hydrogen sulfide bioavailability in biological or other samples.

This method has significant advantages for easy measurement and diagnosis of hydrogen sulfide toxicity levels, including precise analytical measurements of hydrogen sulfide in all of the bioavailable pools, that provides for dose exposure monitoring and diagnosis of hydrogen sulfide toxicity. This analytical method may also be used in measuring hydrogen sulfide and its volatile chemical burden in the environment, including but not limited to, animals, plants, soil, water sources, microbes, and other sources.

BRIEF DESCRIPTION OF THE DRAWINGS

FIG. 3A illustrates the differences in plasma free $H_2S$ between the two different collection tubes (lithium heparin and EDTA collection tubes) as compared to lysed red blood cells (RBC) ($p<0.01$ versus lithium heparin collection tubes). FIG. 3B illustrates amount of cell free hemoglobin in plasma from blood collected in the two different collection tubes as compared to that in lysed red blood cells ($p<0.01$ versus lithium heparin collection tubes).

FIG. 5A illustrates the effect of time on trapping $H_2S$ using an alkaline buffer on hydrogen sulfide recovery. FIG. 5B illustrates the hydrogen sulfide recovery in samples before the release of $H_2S$ and after the release and trap of $H_2S$. FIG. 5C illustrates the effect of time on the release and trapping of sulfide from plasma.

FIG. 6A illustrates the measured sulfide level comparing samples trapped with plasma remaining in the reaction vessel and samples trapped after removal of plasma. FIG. 6B illustrates the change in persulfide over time from incubating plasma with sodium sulfide. FIG. 6C illustrates the protein persulfide concentration in plasma samples with and without the addition of KCN (potassium cyanide).

FIG. 7A illustrates the change in released and trapped H2S in sodium sulfide samples with and without 50 mM TCEP. FIG. 7B illustrates the change in released and trapped $H_2S$ in sodium sulfide samples with and without 1 mM TCEP. FIG. 4C illustrates the effect of incubation time with TCEP on the reduction of diallyl trisulfide (DATS) and subsequent measurement of released $H_2S$ using the MBB method. FIG. 7D illustrates the efficiency of the protocol including reducing, releasing, and trapping using samples with sodium sulfide, DATS or both and with or without 1 mM TCEP. FIG. 7E shows the effect of TCEP on stability of the MBB method product sulfide dibimane at pH 9.5 and pH 4.5.

FIG. 8A illustrates the sulfide level in the three sulfide pools in blood samples taken from wild-type C57Bl/6J mice as compared to cystathimine-γ-lyase (CSE) knockout mice (CSE−/−), known to be defective in hydrogen sulfide production. FIG. 8B illustrates the sulfide level in the three sulfide pools in blood samples from healthy male human controls.

MODES FOR CARRYING OUT THE INVENTION

Figure 1:
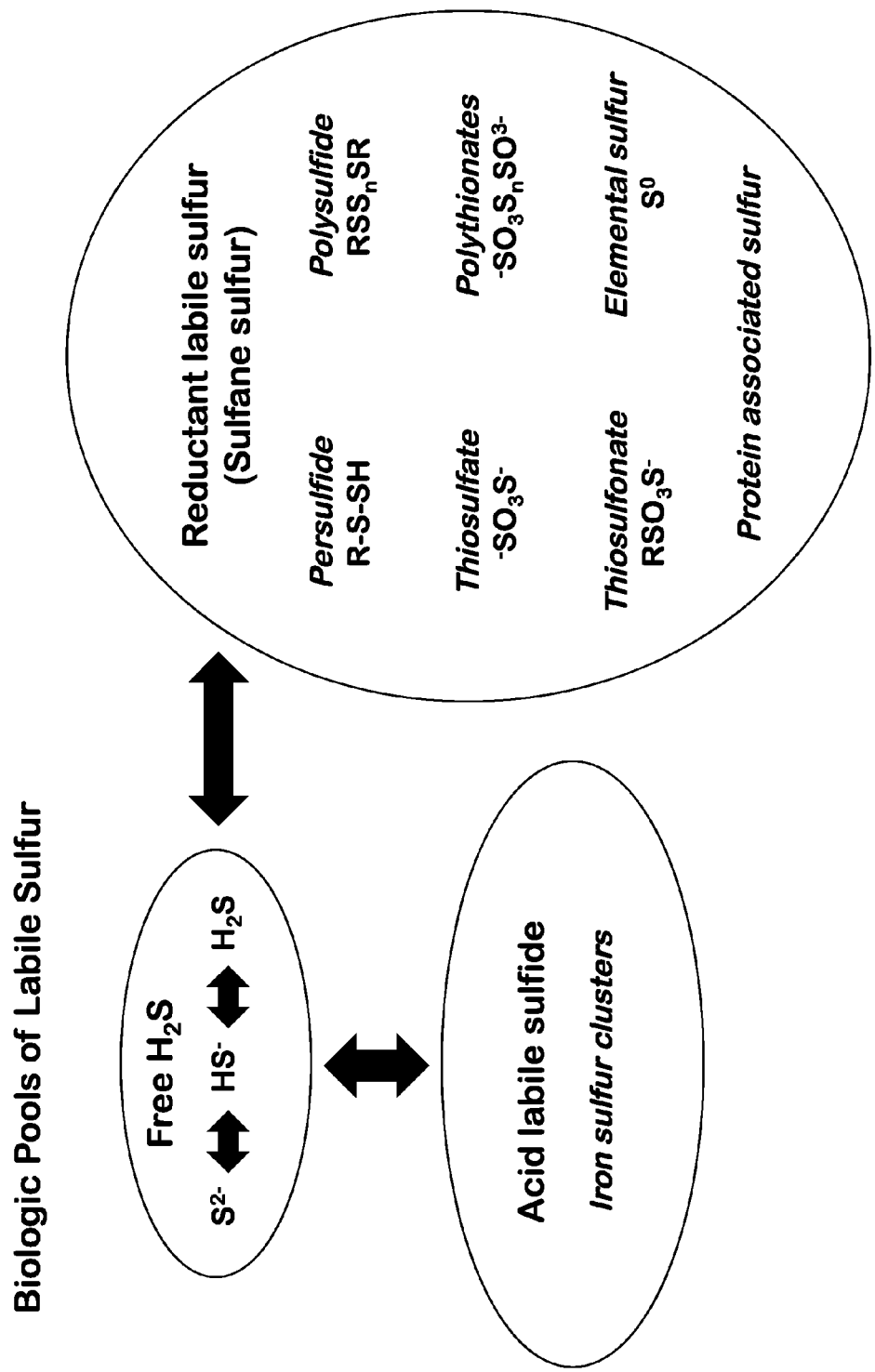
FIG. 1 illustrates the three biological pools of labile sulfide found in organisms.
Figure 2:
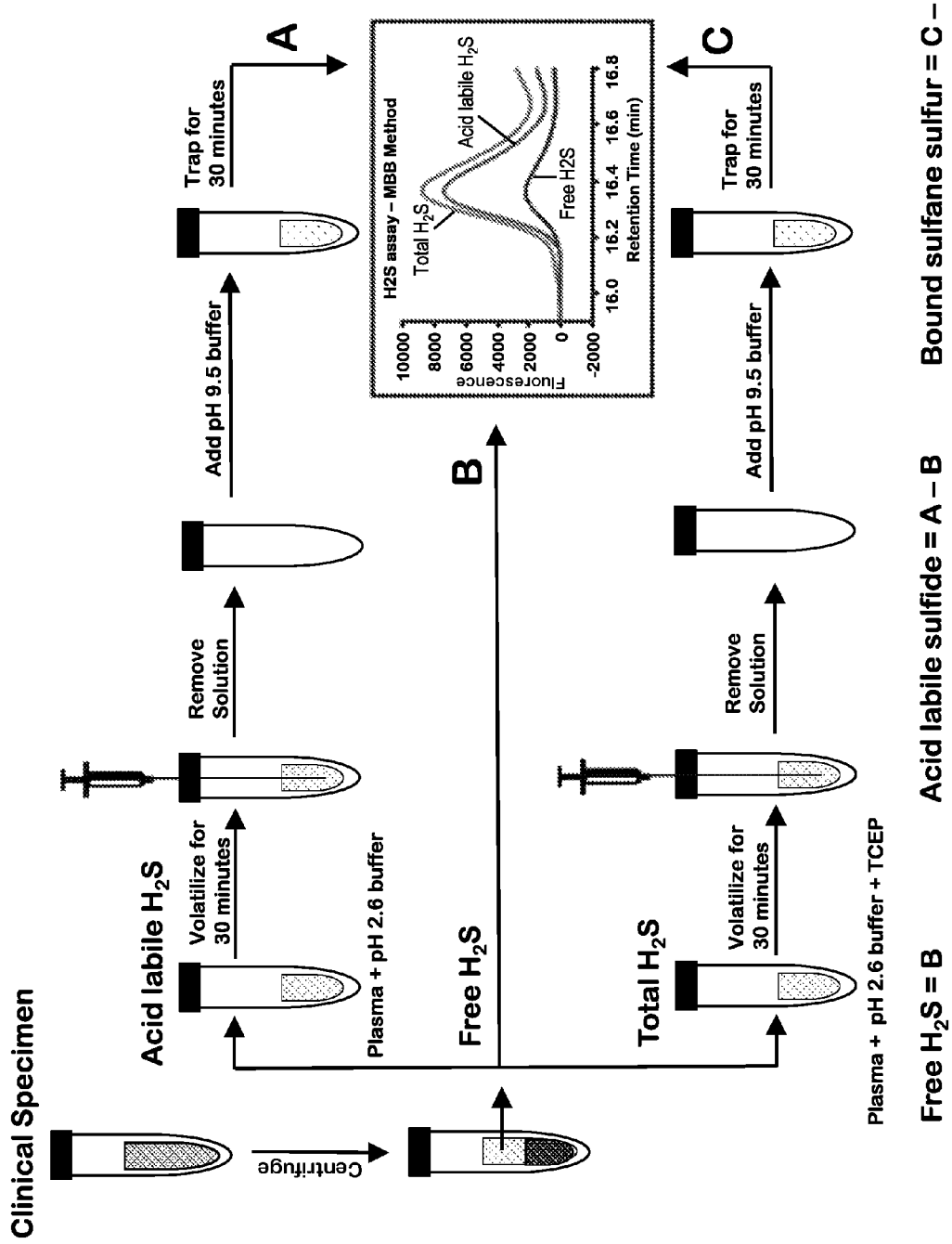
FIG. 2 is a schematic overview of one embodiment of the method to measure the three pools of labile sulfide: free $H_2S$, acid-labile sulfide, and bound sulfane sulfur.

The fluorescent reagent MBB has been widely used to measure various thiol-containing species through alkylation [22]. S-alkylation occurs twice with sulfide under alkaline conditions, forming sulfide-dibimane. We have previously reported an analytical method of measuring free plasma hydrogen sulfide in vivo and in vitro by derivatization of sulfide with an excess of monobromobimane under alkaline, 1% oxygen, trace metal-free conditions with RP-HPLC separation and fluorescent detection of the sulfide-dibimane product [18]. Free or volatilized hydrogen sulfide is derivatized in alkaline conditions, preferably pH>7.5, more preferably about pH 8.0 to about pH 10.0, and most preferably, about pH 9.5. The derivatization should occur under low oxygen conditions, preferably ≤5% oxygen, more preferably <2% oxygen, and most preferably ≤1% oxygen. In addition, any trace metals should be chelated to avoid any interference in the reaction. In the methods below, we used diethylenetriaminepentaacetic acid (DTPA) to chelate trace metals. In addition, we used excess MBB, at about a ratio of 2:1 for MBB to sulfide. The derivatization reaction is stopped after about 30 min with acid (pH<5), for example, with sulfosalicylic acid, at about pH 4.5, to stabilize the SDB product and to precipitate any proteins. The SDB product was then analyzed with RP-HPLC, and compared with standards to give the concentration.

The release of hydrogen sulfide from the acid labile pool requires a pH less than 5.4 [11]. Thus the determination of acid labile sulfide involves acidification of the sample, preferably pH<4.0, more preferably from about pH 2.0 to about pH 3.0, and most preferably about pH 2.6. In the experiments below, the acid solution was 100 mM phosphate buffer (30 µM of $H_3PO_4$ and 70 µM of $KH_2PO_4$, pH 2.6, 0.1 mM DTPA) causing release of free hydrogen sulfide into the headspace of the closed (e.g., vacutainer) tube from the acid labile pool. After removal of the original solution to prevent interference from any proteins, an alkaline solution was added to trap and re-dissolve the $H_2S$ gas. The measurement of the sulfide then proceeds as discussed above for the free $H_2S$. The sulfide concentration from this procedure reflects both free hydrogen sulfide and hydrogen sulfide released from the acid labile pool.

The total labile sulfide amount, including the sulfane sulfur component along with the acid-labile and free sulfide, is determined by using a reducing compound with the acid solution reported above for the acid-labile result. The reducing agent we have used was tris (2-carboxyethyl) phosphine hydrochloride (TCEP), which cleaves disulfide bonds to liberate the sulfane sulfur atom. While dithiothreitol (DTT) could also be used, TCEP is preferred because it is water soluble, non-volatile, reduces disulfide bonds more rapidly and has been shown to be very stable across a wider range of pH (2.0-9.5) than DTT. TCEP does not have a thiol moiety and has the additional advantage of not requiring thiol removal prior to reaction with MBB. By contrast DTT contains a thiol moiety and has been reported to have small amounts of sulfide contaminants [21].

However, reductive de-halogenation of monobromobimane by TCEP with the creation of a fluorescent product has been reported with the potential for interference [25]. While this product can be extracted by methylene chloride, it is not necessary in our method, because HPLC analysis of the reaction mixture separated this product from sulfide-dibimane. We found that the product of TCEP and MBB has a retention time of 11.2 min (data not shown), whereas the product of sulfide and MBB, i.e. sulfide-dibimane has a retention time of 16.5 min, and MBB alone has a retention time of 17.6 min. To overcome TCEP consumption of MBB as well as any inhibitory effects on the dye, as has been reported with iodoacetamide and maleimide dyes [26], we used a ratio of greater than 10:1 MBB to TCEP.

Persulfide formation normally occurs at alkaline pH at room temperature, and persulfide can be measured by absorbance at 335 nM using a spectrophotometer [27]. Free hydrogen sulfide released into the headspace can react with plasma proteins to form persulfide as reported below using spectrophotometry. Thus, removal of plasma (or other sample) from the reaction vessel after volatilization of hydrogen sulfide into the headspace is preferred prior to re-trapping the volatilized hydrogen sulfide gas in alkaline solution for subsequent reaction with MBB.

The use of this protocol in both experimental and clinical specimens will enable measurement of hydrogen sulfide bioavailable equivalents during pathophysiological events and provide a critical analytical detection method for pharmacologic endeavors to manipulate the levels of hydrogen sulfide for therapeutic purposes. The method can also be used to measure sulfide from environmental water samples.

Example 1

Materials and Methods

Materials:

Throughout these experiments, we used monobromobimane (MBB, Sigma-Aldrich, St. Louis, Mo.; Cat. No. B4380); sodium sulfide (Alfa Aesar, Ward Hall, Mass., Cat. No. 65122), which has been demonstrated to have superior purity compared to other sources [8]; microtainer plasma separator tubes (BD Biosciences, San Jose, Calif., Cat. No. 365958); sulfosalicylic acid (SSA, Sigma-Aldrich, Cat. No. S2130); Acetonitrile (CH3CN, Sigma-Aldrich, Cat. No. 34851); Trifluoroacetic acid (TFA, Thermo Fisher Scientific, Waltham, Mass., Cat. No. 28903); BD Vacutainer (Becton Dickinson and Company (BD), Franklin Lakes, N.J., Cat. No. 366703); 1 ml plastic syringe; PCR tube (Molecular Bioproducts, San Diego, Calif., Cat. No. 34129); 3.5 inch 25 gauge spinal needle (BD #405180); and, ½ inch 30 gauge needle (BD #305106). All collection tubes (vacutainer tubes with lithium heparin or EDTA) were plastic to avoid $H_2S$ binding to glass. Unless otherwise stated, all other reagents were purchased from Sigma-Aldrich.

Instrumentation.

Throughout these experiments, we used Pan mass balance (0.1 mg sensitivity) (Mettler; AG104); Vortex mixer (Thermolyne; Maxi Mix II); SmartSpect™ Plus Spectrophotometer (Bio-RAD); HPLC system: Shimadzu Prominence ultrafast liquid chromatography (UFLC) equipped with fluorescence detector (HPLC 20A Prominence); hypoxic chamber (Coy Laboratory Products Inc., Grass Lake, Mich.; large glove box); and Nutating mixer (VWR, Radnor, Pa.; S0500).

Animals and Human Subjects.

The wild-type C57Bl/6J mice were commercially purchased (The Jackson Laboratory, Bar Harbor, Me.), and the CSE knockout mice (CSE−/−) were from Dr. Rui Wang, Lakehead University (Thunder Bay, Ontario, Canada). The use of mice for this study was approved by the Institutional Animal Care and Use Committee of the Louisiana State University (LSU) Health Shreveport, Shreveport, La. All animals received humane care in compliance with regulations. The enrollment of male healthy human subjects was approved by the Institutional Review Board of the Louisiana State University (LSU) Health Shreveport, Shreveport, La. The human subjects were males between 23-34 years of age.

Sample Preparation and Detection for Free Hydrogen Sulfide [18].

The method was similar to that previously reported [18]. In brief, BD microtainer plasma separator tubes with lithium heparin for murine samples and plastic BD vacutainer with lithium heparin for human samples were placed on ice. Lithium heparin was used as the anticoagulant because it has been shown to be less prone to cause hemolysis than EDTA [32; and results below]. Blood was collected using plastic syringes or plastic capillary tubes directly into plasma separator tubes, especially avoiding use of glass syringes. The blood was placed in the tubes, and the tubes were centrifuged at 3000 RCF for 2 minutes at 4° C. for the murine samples and at 1500 RCF for 4 minutes at 4° C. for the human samples. Throughout these experiments, all samples were maintained at 4° C. to minimize enzymatic production or degradation of hydrogen sulfide, and the binding of $H_2S$ to the experimental vessels was minimized by using polypropylene reaction vessels. Derivatization reaction of sulfide with monobromobimane was performed at 1% $O_2$ in a hypoxic chamber by transferring 30 μl of plasma, 70 μl of Tris-HCl (100 mM, pH 9.5, 0.1 mM DTPA) and 50 μl of MBB solution (10 mM, in $CH_3CN$) into the PCR tube. Regarding the measurement of hydrogen sulfide, derivatization was performed in the dark because MBB is a light sensitive reagent. Additionally, a 1% oxygen environment was maintained throughout the reaction protocol with acid and reducing agents, as well as the MBB reaction process.

The MBB mixture was incubated at room temperature for 30 min, and then stopped by adding 50 μl of 200 mM ice-cold sulfosalicylic acid solution (to stop the reaction and precipitating protein) and vortexed for 10 sec. The tubes were placed on ice for 10 min, and then centrifuged at 12,000 rpm at 4° C. for 10 min. After centrifugation, 10 μl of the supernatant was injected into an RP-HPLC system with an Agilent Eclipse XDB-C18 column (5 μm, 80 Å, 4.6 mm×250 mm) equilibrated with 15% $CH_3CN$ in water that contained 0.1% (v/v) TFA. Fluorescence detection was set at 390 nm (excitation) and 475 nm (emission). Monobromobimane and sulfide-dibimane were separated using the gradient of two mobile phases identified in Table 1 (Phase A: water containing 0.1% (v/v) TFA; and Phase B: 99.9% $CH_3CN$, 0.1% (v/v) TFA) at a flow rate of 0.6 mL/min. The retention times for the sulfide-dibimane and the monobromobimane peaks were 16.5 and 17.6 minutes, respectively. The amount of hydrogen sulfide was measured from linear plots of the HPLC peak areas of sulfide-dibimane versus known concentrations of sulfide solution.

TABLE 1

Mobile Phase Gradient Table

| Time(min) | % Phase A | % Phase B |
|---|---|---|
| 0 | 85 | 15 |
| 5 | 65 | 35 |
| 16 | 45 | 55 |
| 23 | 30 | 70 |
| 24 | 10 | 90 |
| 26 | 10 | 90 |
| 28 | 85 | 15 |

Sample Preparation and Detection of Hydrogen Sulfide in the Acid Labile Pool.

The release of hydrogen sulfide from the acid labile pool requires a pH less than 5.4 [11]. Thus, the determination of acid-labile sulfide involves acidification of the sample, 50 μl plasma, performed by adding 450 μl of 100 mM phosphate buffer (30 μM of $H_3PO_4$ and 70 μM of $KH_2PO_4$, pH 2.6, 0.1 mM DTPA) causing release of free hydrogen sulfide into the headspace of a vacutainer tube from the acid-labile pool. After incubation for 30 min, the solution is removed to remove any plasma proteins, and 100 mM Tris-HCl buffer (pH 9.5, 0.1 mM DTPA) is added to re-dissolve the hydrogen sulfide gas back into the buffer. Then the protocol proceeds as described above with the addition of MBB, and measuring the sulfide level by the MBB method as described above. The sulfide concentration so determined reflects both free hydrogen sulfide and hydrogen sulfide released from the acid labile pool. The concentration of acid-labile sulfide can be calculated by subtracting the free $H_2S$ pool result from the acid-labile result.

Sample Preparation and Detection of Hydrogen Sulfide in the Sulfane Component.

The sulfane sulfur component is determined by initially treating a 50 μl plasma sample with 450 μl of 100 mM phosphate buffer (30 μM of H3PO4 and 70 μM of KH2PO4, pH 2.6, 0.1 mM DTPA; 1 tris (2-carboxyethyl) phosphine hydrochloride (TCEP)). The TCEP cleaves disulfide bonds to liberate the sulfane sulfur atom. Then the sample is incubated for 30 min, and the solution removed, and processed as described above for the acid-labile component. Reductive de-halogenation of monobromobimane by TCEP with the creation of a fluorescent product has been reported with the potential for interference [25]; while this product can be extracted by methylene chloride, it is not necessary since HPLC analysis of the reaction mixture separates this product from sulfide-dibimane. To overcome TCEP consumption of MBB as well as any inhibitory effects on the dye as has been reported with iodoacetamide and maleimide dyes [26], a ratio of greater than 10:1 MBB to TCEP was used. Then the protocol proceeds as described above with the addition of MBB, and measuring the sulfide level by the MBB method as described above. The resulting sulfide concentration reflects the total amount of free hydrogen sulfide and the hydrogen sulfide released from both the acid labile pool and the bound sulfide pool. The sulfide concentration from the bound sulfane pool can be calculated by subtracting the acid-labile result from this result.

Example 2

Optimizing Protocol for Measurement of Free $H_2S$

Figure 3A:
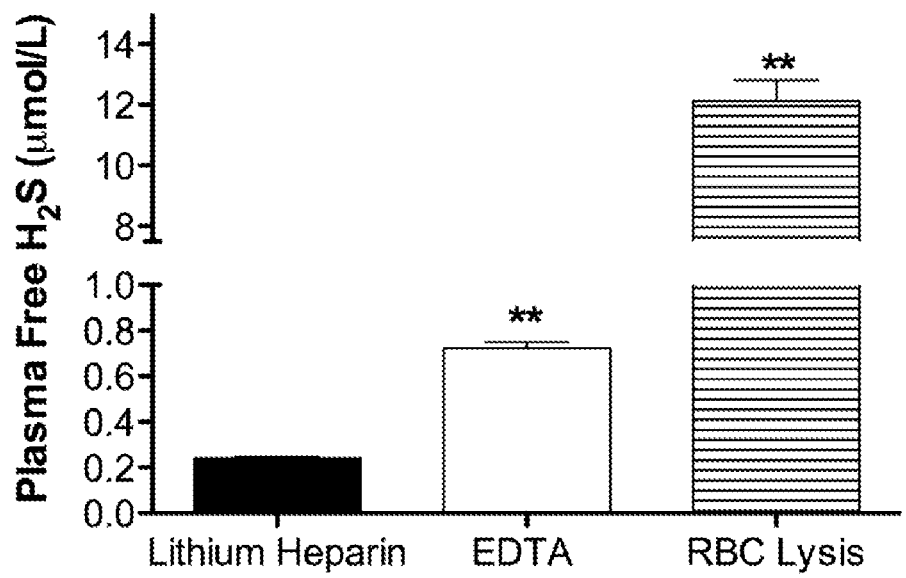
FIGS. 3A and 3B illustrate the effect of blood collection tubes on plasma $H_2S$ levels.
Figure 3B:
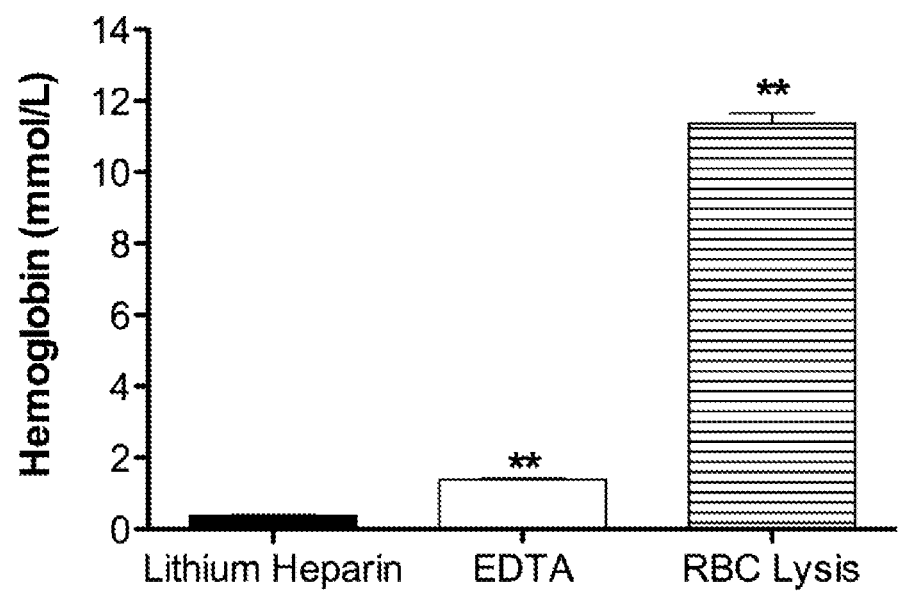

Lithium heparin collection tubes were selected after preliminary experiments using healthy blood human donors had demonstrated that lithium heparin tubes decreased hemolysis as compared to EDTA collection tubes. For this test, venous blood was collected from healthy volunteers in either lithium heparin or EDTA vacutainer collection tubes, and the plasma free $H_2S$ was measured as described above. FIG. 3A depicts the differences in plasma free $H_2S$ between the different collection tubes versus lysed red blood cells (RBC) ($p<0.01$ versus lithium heparin collection tubes). To ensure consistency, the lithium heparin collection tubes were thereafter used throughout. FIG. 3B illustrates amount of cell free hemoglobin measured using the Drabkin assay in plasma from blood collected in various tubes versus lysed red blood cells ($p<0.01$ versus lithium heparin collection tubes). Again the lithium heparin tubes showed less cell lysis.

Figure 4:
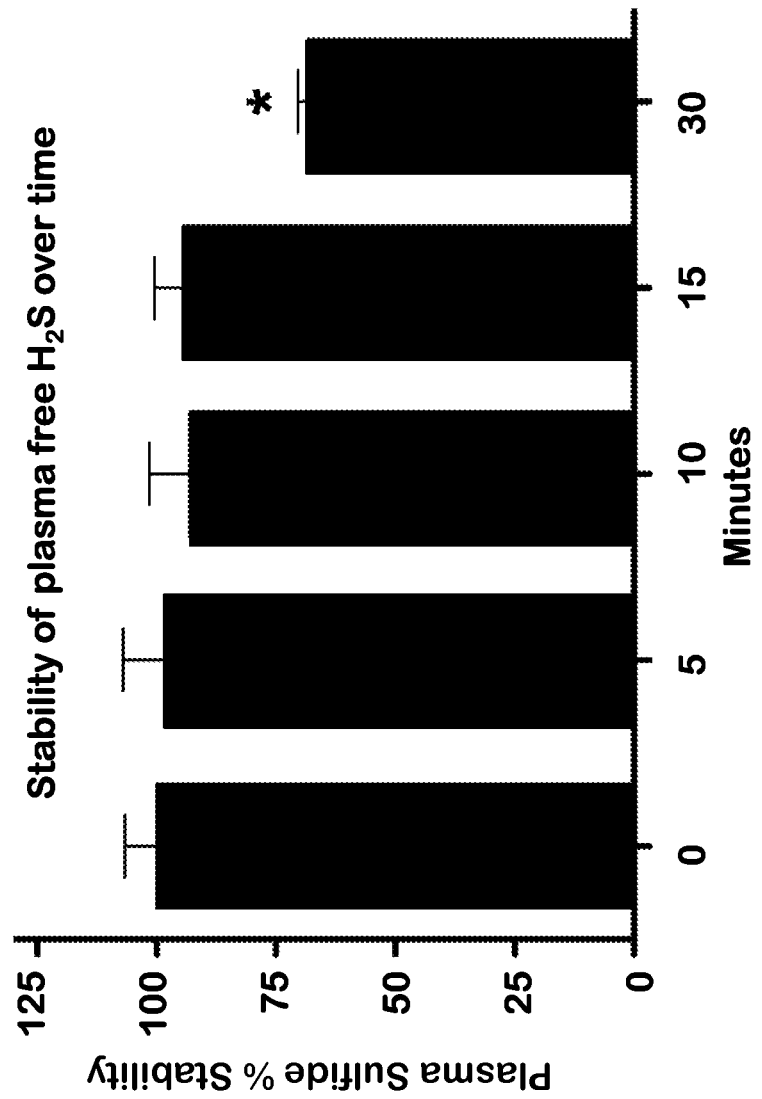
FIG. 4 illustrates the stability of plasma free $H_2S$ as a function of time.

In addition, the stability of plasma free $H_2S$ was measured as a function of time after collection. Venous blood was collected in lithium heparin vacutainer tubes and incubated on ice for various times. Free plasma $H_2S$ was measured at each time point as described above, and the results are shown in FIG. 4. The results were compared with one way ANOVA with Bonferroni post-test to the 0 minute time point, *$p<0.05$ versus all time points. A significant reduction in $H_2S$ was seen only in the 30 min sample.

Example 3

Figure 5A:
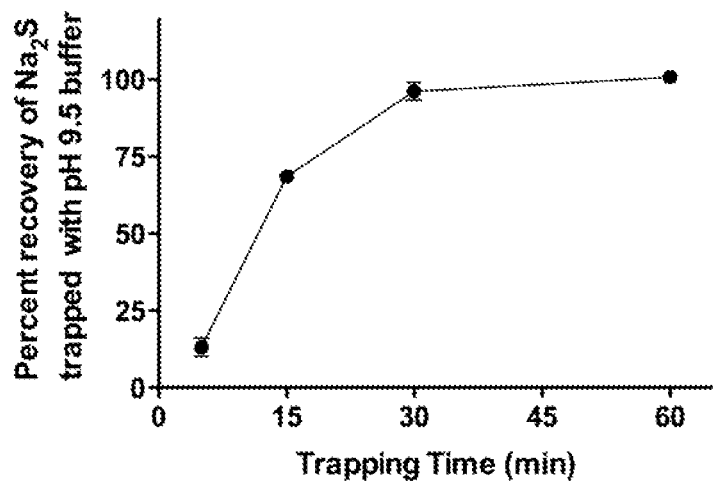
FIGS. 5A-5C illustrate the optimization of the measurement techniques for the measurement of the volatilized $H_2S$ using sodium sulfide and an acid buffer to initially generate $H_2S$.

Optimizing Efficiency of Detection for Acid-Labile Sulfide and Bound Sulfane Sulfur To establish the efficiency of the acid liberation technique and alkaline Tris-HCl buffer trapping of the headspace sulfide gas, the optimal trapping time was determined with a known molar solution of sodium sulfide. FIG. 5A shows the effect of trapping time on hydrogen sulfide recovery. After 50 µL of 40 µM sodium sulfide was incubated with 450 µL of 0.1 M pH 2.6 phosphate buffer for 30 min, hydrogen sulfide gas was re-trapped by 500 µL of 0.1 M Tris-HCl buffer (pH 9.5, 0.1 mM DTPA), and then measured with the MBB method described above. As shown in FIG. 5A, the highest recovery percentage was achieved after 30 min of trapping headspace sulfide gas, establishing this time-frame as optimal.

Figure 5B:
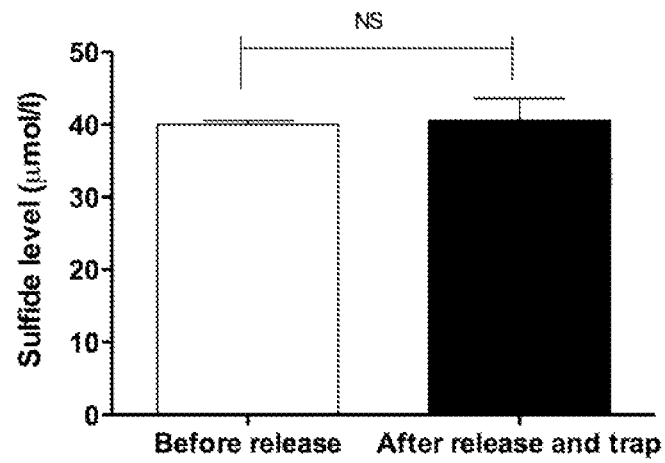

Next, the effect of sodium sulfide release and re-trapping was examined on hydrogen sulfide recovery, and the results are shown in FIG. 5B. The hydrogen sulfide detected from 40 µM of sulfide was compared before release and after releasing and trapping times were 30 min. FIG. 5B shows that the percentage recovery of acid volatilized hydrogen sulfide was optimal both where the sulfide content of a known molar solution of sodium sulfate was measured directly, and after acid release and alkaline re-trapping.

Figure 5C:
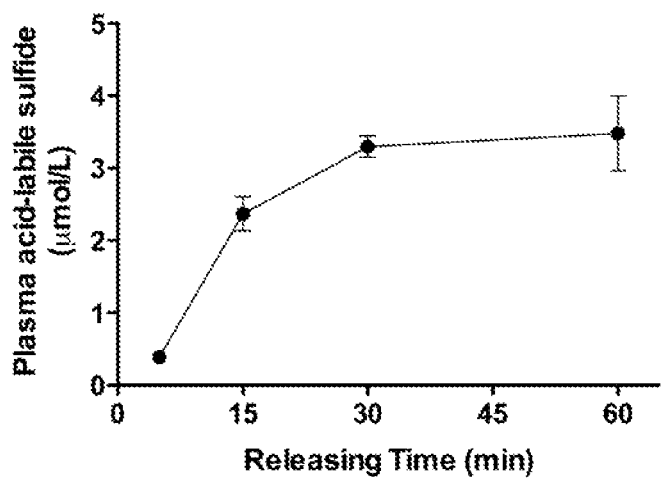

The optimal time for release of hydrogen sulfide after acidification of plasma was determined, and the results are shown in FIG. 5C. 50 µL of plasma was incubated with 450 µL of 0.1M pH 2.6 phosphate buffer for different lengths of time and then re-trapped for 30 min, demonstrating optimal release at 30 min. Therefore, 30 min of releasing time and 30 min of trapping time were applied in all of the subsequent experiments. Furthermore, the residual hydrogen sulfide in the plasma after volatilization by acidification was measured and found to be 0.0125+/−0.0029 µM, which was slightly above the reaction solution background level, which was 0.00725+/−0.0018 µM. This does not represent a significant fraction of $H_2S$ detected in the headspace after acid volatilization.

Example 4

Effect of Plasma Protein on Trapping Volatilized Hydrogen Sulfide

To test the interaction of plasma proteins with the released hydrogen sulfide in the headspace of the vacutainer tube during alkaline re-trapping, the amount of hydrogen sulfide detected when the plasma was retained in the vacutainer tube was determined and compared to the amount when the plasma was removed. In addition, the formation of persulfides was measured in the plasma. After centrifugation, 50 µl of plasma was added separately into two sets of 4 ml BD vacutainer tubes. 450 µl of 100 mM phosphate buffer (pH 2.6, 0.1 mM DTPA) was added to these tubes, and the tubes were incubated on the nutating mixer for 30 min. In one tube, solution was removed through the cap with a 25 gauge spinal needle and 1 ml plastic syringe, and then 500 µl of 100 mM Tris-HCl buffer (pH 9.5, 0.1 mM DTPA) was added into the BD vacutainer tube. In the other tube, 25 µl of 3M NaOH solution was added to adjust the pH to ~9.5. Then the tubes were incubated for 30 min on the nutating mixer. The sulfide levels in the BD vacutainer tubes were measured by the MBB method as described above. Also, 20 µl of the samples were mixed with 200 µl of 100 mM KCN (dissolved into 10 mM NaOH), and then $A_{335}$ was measured [28], and further development of a red color was facilitated by adding 200 µl of ferric nitrate solution (dissolved 2 g of $Fe(NO_3)$, 9 ml $H_2O$ in 20 ml of 65% nitric acid) [29]. Similarly, 0, 30, or 300 µM of $Na_2S$ (final concentration) was incubated with the mixture of plasma and 0.1 M Tris-HCl buffer (pH 9.5, v/v 1:9) under hypoxic conditions (1% $O_2$), and the $A_{335}$ was measured by spectrophotometry at 0, 10, 30, and 60 min as previously described [30].

Figure 6A:
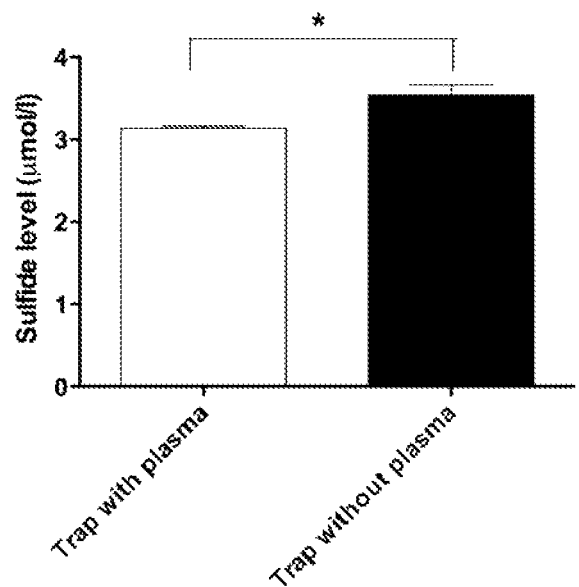
FIGS. 6A-6C illustrate the effect of the presence of plasma proteins on trapping hydrogen sulfide gas.
Figure 6B:
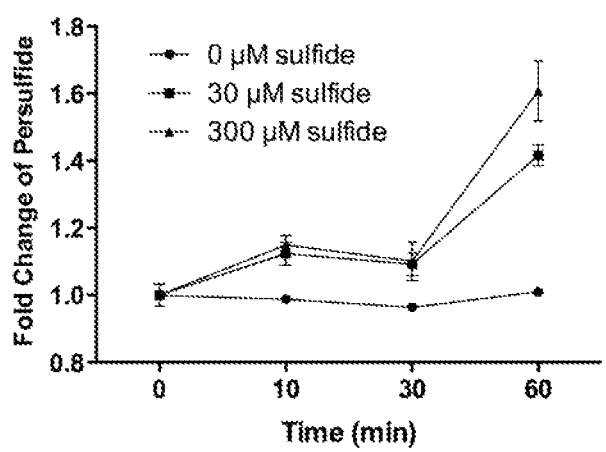
Figure 6C:
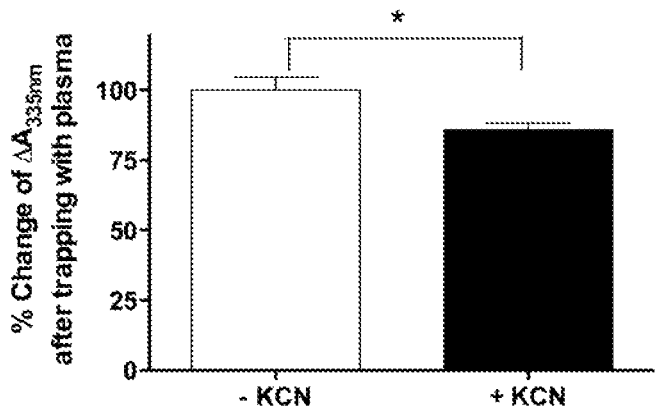

FIGS. 6A-6C show the effect of plasma proteins on trapping hydrogen sulfide gas. FIG. 6A shows a comparison of sulfide level between samples trapped with plasma remaining in the reaction vessel and samples trapped after removal of plasma. After 50 µL of plasma was incubated with 450 µL, of 0.1M pH 2.6 phosphate buffer for 30 min, in the first group ~25 µL of 3 M NaOH solution was added directly to plasma to adjust pH to 9.5, and then trapped for 30 min. In the second group, the plasma was removed from the reaction vessel, and the released hydrogen sulfide was trapped by 500 µL of 0.1 M Tris-HCl buffer, pH 9.5, for 30 min. The sulfide was then measured using the MBB method. As shown in FIG. 6A, the measured hydrogen sulfide decreased when the trapping process occurred while the plasma remained in the reaction vessel, as opposed to removal and replacement with the 100 mM Tris-HCl (pH 9.5) buffer.

Throughout these experiments, the volatilization of hydrogen sulfide from the samples was accomplished by the immediate collection of the samples into vacuum tubes that were maintained at all times without plasma after volatilization, and the transfer of the reagents and solutions was done via a needle inserted into the rubber stop-cock of the vacuum tubes in order to avoid the loss of vacuum and gas samples [31]. The loss of hydrogen sulfide in the presence of plasma was attributed to the formation of protein persulfides, by measurement of persulfide formation using the cyanolysis method compared to known molar concentrations of sodium sulfide reacted with plasma (FIGS. 6B and 6C).

FIGS. 6B and 6C show the effect of sulfide on protein persulfide formation. For FIG. 6B, 0, 30, 300 µM of sodium sulfide was incubated with plasma and the resulting generation of persulfide was measured at various time points. In FIG. 6C, the effect of sulfide on protein persulfide formation was measured. Samples trapped with plasma with and without added KCN was measured for persulfide formation by measuring absorbance at 335 nm.

Example 5

Effect of TCEP on Hydrogen Sulfide Reaction with Monobromobimane

Figure 7A:
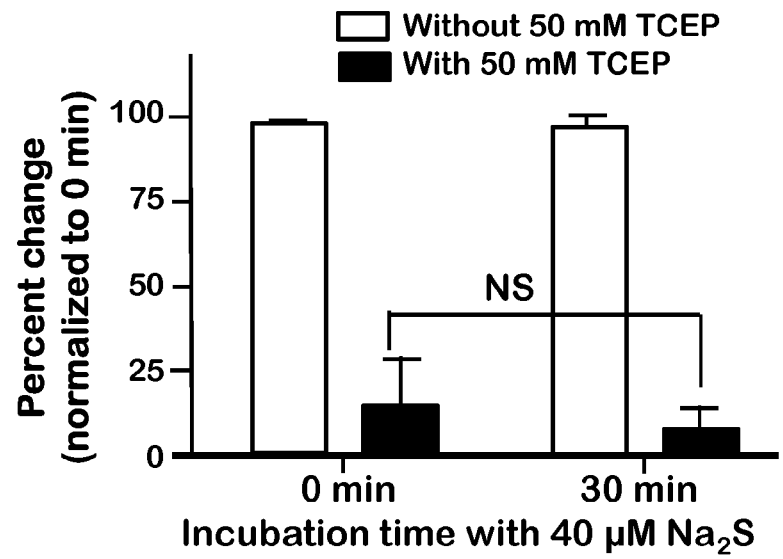
FIGS. 7A-7E illustrate the optimization of the method to measure total sulfide using TCEP as the reducing agent and showing changes in measurements of released hydrogen sulfide using the MBB method.
Figure 7B:
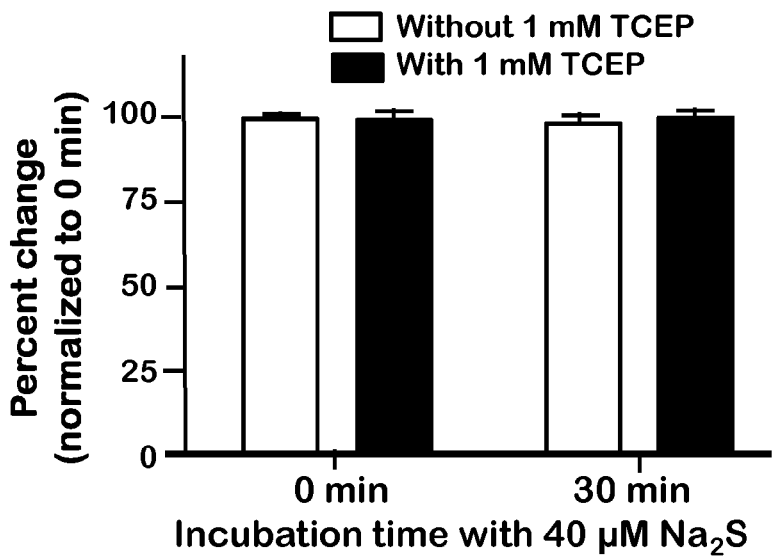

Since TCEP is a strong reducing agent that can react with MBB, the effect of different concentrations of TCEP on sulfide derivatization was analyzed. A 100 mM TCEP stock solution in $H_2O$ was prepared. The respective final concentrations of TCEP (1 and 50 mM) were incubated with 20 µM sodium sulfide for 10 min. 30 µl of the TCEP/sodium sulfide sample was transferred into a PCR tube with 70 µl of reaction buffer (100 mM Tris-HCl, 0.1 mM DTPA, pH 9.5). Then 50 µl of 10 mM MBB solution was added, and the mixture incubated for 30 min at 1% $O_2$ in the hypoxic chamber at room temperature. 50 µl of 200 mM SSA solution was added to stop the reaction, and 10 µl of the reaction solution was used for RP-HPLC analysis to measure sulfide concentration. Before sulfide derivatization, 50 mM or 1 mM TCEP was added to the sulfide stock solution containing 40 µM sodium sulfide. As shown in FIGS. 7A and 7B, TCEP affected the sulfide-monobromobimane reaction in the presence of 50 mM TCEP, but there was not a significant effect in the presence of 1 mM TCEP.

Figure 7C:
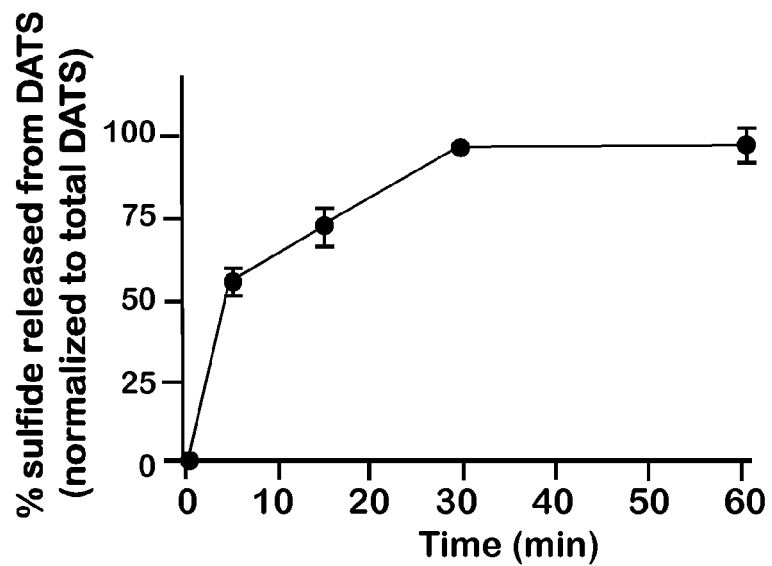
Figure 7D:
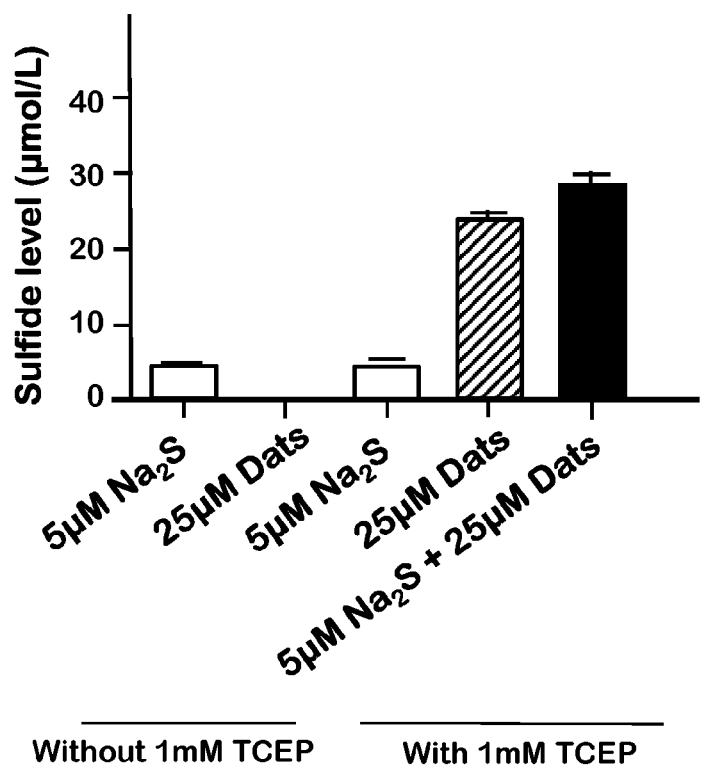

Diallyl trisulfide (DATS) is an organic polysulfide compound that acts as a sulfide donor. DATS was used to verify the efficiency of TCEP reduction of the disulfide bonds. The effect of TCEP on diallyl trisulfide (DATS) reduction was analyzed using 50 µL of 25 µM DATS incubated with 450 µL of 0.1 M phosphate buffer (pH 2.6, 1 mM TCEP) at different time points, and the resulting hydrogen sulfide was trapped with 0.1M Tris-HCl buffer for 30 min. As shown in FIG. 7C, 95% of DATS was reduced to free sulfide after incubation with 100 mM phosphate buffer (pH 2.6, 0.1 mM DTPA and 1 mM TCEP) for 30 min. To test the efficiency of the protocol including reducing, releasing and trapping, 5 µM $Na_2S$ and 25 µM DATS were used with and without TCEP. As shown in FIG. 7D, DATS was demonstrated to be stable in the absence of TCEP, but with TCEP there is complete reduction of and an expected release of hydrogen sulfide using 100 mM phosphate buffer (pH 2.6, 0.1 mM DTPA and 1 mM TCEP) for 30 min. This was demonstrated both with and without the presence of 5 µM sodium sulfide plus 25 µM DATS.

Example 6

Stability of Sulfide-Dibimane

Figure 7E:
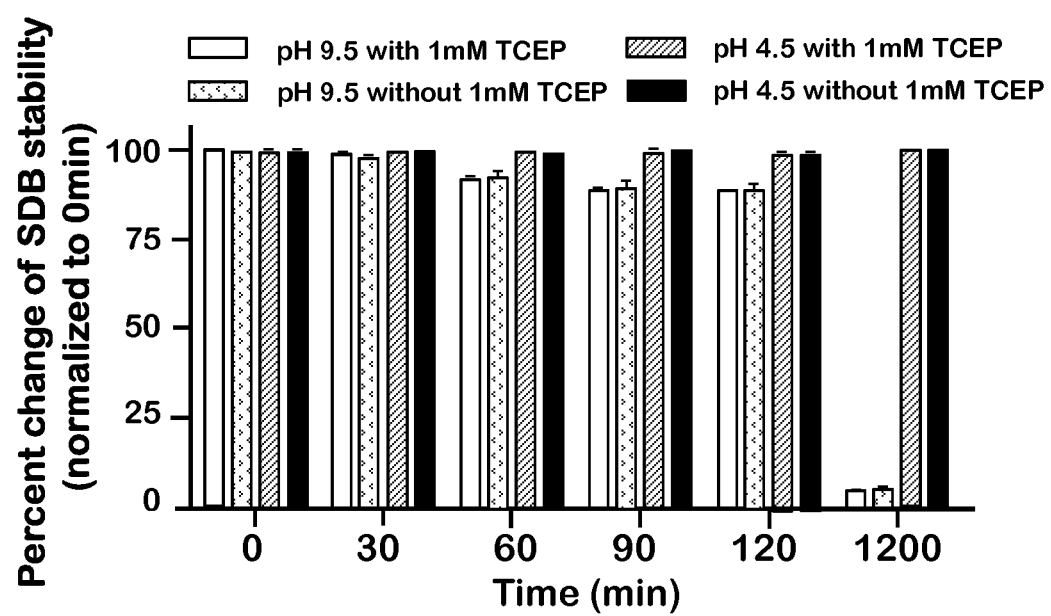

The stability of the sulfide-dibimane product in the presence of TCEP was examined. Two solutions were prepared at pH 4.5 and at pH 9.5, respectively, and a 12 µM sulfide-dibimane solution was prepared using the two different pH solutions. The mixtures were treated with or without 1 mM TCEP. At various time points, aliquots (200 µl each) of these solutions were withdrawn and analyzed by RP-HPLC. The reaction between hydrogen sulfide and MBB occurred under alkaline conditions using the buffer described above (pH 9.5), and was then terminated and stabilized with 200 mM sulfosalicylic acid. As shown in FIG. 7E, hydrolysis of the SDB was increased at pH 9.5 in the presence of 1 or 0 mM TCEP, with only 5% SDB remaining after a 20-h incubation. However, in the acid buffer, SDB was stable at 4° C. in the presence of 1 or 0 mM TCEP.

Example 7

Figure 8A:
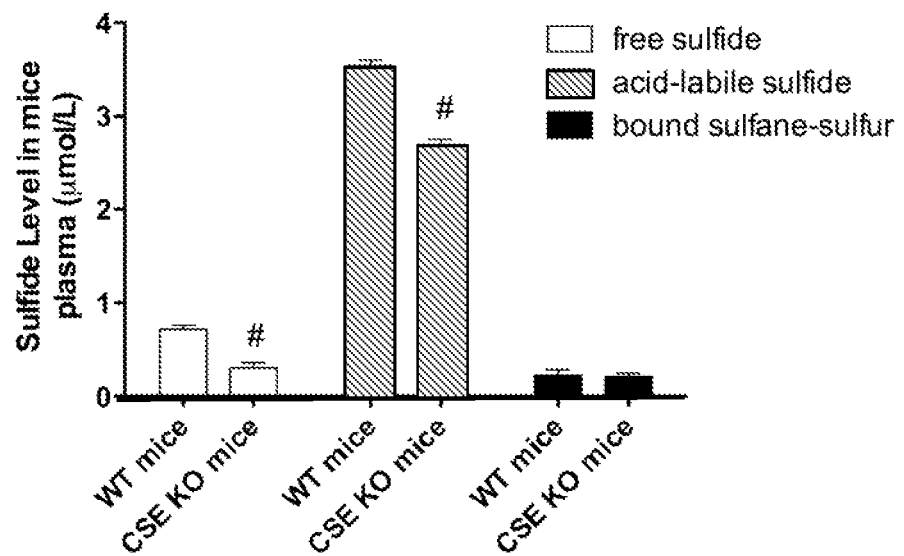
FIGS. 8A-8B illustrate the levels of free hydrogen sulfide, acid-labile sulfur, and bound sulfane-sulfur in murine and human plasma.
Figure 8B:
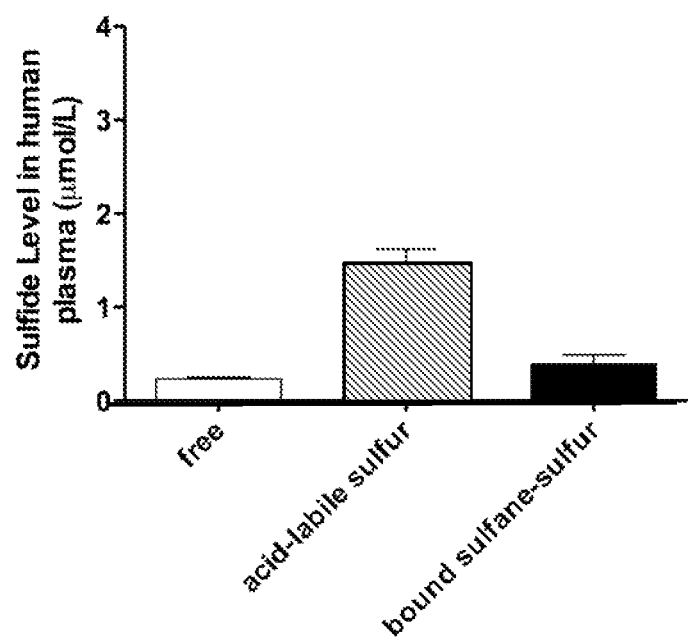

Comparison of Free Sulfide, Acid-Labile Sulfide, and Bound Sulfane Sulfur in Murine and Human Plasma Samples Free hydrogen sulfide, acid-labile sulfide and bound sulfane sulfur levels were measured in the plasma of wild type C57BL/6J mice (WT mice), CSE gene deficient mice (CSE KO mice) and healthy human volunteers. As shown in FIG. 8A, the CSE knockout mice, known to be defective in hydrogen sulfide production, showed a significant decrease in free and acid-labile sulfide compared to wild-type mice, but showed no significant difference in bound sulfane sulfur (FIG. 8A). In the human samples, the highest pool was the acid-labile pool with low amounts of both free hydrogen sulfide and bound sulfane sulfur. (FIG. 8B). The higher levels of the acid labile pool in plasma from both mice and humans in contrast to the lower levels of free hydrogen sulfide support the theory of the acid-labile pool as a reversible sulfide sink, into and from which hydrogen sulfide can be stored or released to effect biologic function.

Thus we have developed a method to measure the concentration of labile hydrogen sulfide from the three main pools of labile hydrogen sulfide: free H2S gas, acid-labile sulfide, and bound sulfane-sulfur.

REFERENCES

[1] Kabil, O.; Banerjee, R. Redox biochemistry of hydrogen sulfide. The Journal of biological chemistry 285:21903-21907; 2010.

[2] Lavu, M.; Bhushan, S.; Lefer, D. J. Hydrogen sulfide-mediated cardioprotection: mechanisms and therapeutic potential. Clin Sci (Loud) 120:219-229; 2011.

[3] Olson, K. R. The therapeutic potential of hydrogen sulfide: separating hype from hope. American journal of physiology 301:R297-312; 2011.

[4] Wang, R. Two's company, three's a crowd: can H2S be the third endogenous gaseous transmitter? The FASEB journal: official publication of the Federation of American Societies for Experimental Biology 16:1792-1798; 2002.

[5] Zhao, W.; Zhang, J.; Lu, Y.; Wang, R. The vasorelaxant effect of H(2)S as a novel endogenous gaseous K(ATP) channel opener. The EMBO journal 20:6008-6016; 2001.

[6] Mathai, J. C.; Missner, A.; Kugler, P.; Saparov, S. M.; Zeidel, M. L.; Lee, J. K.; Pohl, P. No facilitator required for membrane transport of hydrogen sulfide. Proceedings of the National Academy of Sciences of the United States of America 106:16633-16638; 2009.

[7] Dombkowski, R. A.; Russell, M. J.; Olson, K. R. Hydrogen sulfide as an endogenous regulator of vascular smooth muscle tone in trout. American journal of physiology 286:R678-685; 2004.

[8] Hughes, M. N.; Centelles, M. N.; Moore, K. P. Making and working with hydrogen sulfide: The chemistry and generation of hydrogen sulfide in vitro and its measurement in vivo: a review. Free radical biology & medicine 47:1346-1353; 2009.

[9] Kajimura, M.; Fukuda, R.; Bateman, R. M.; Yamamoto, T.; Suematsu, M. Interactions of multiple gas-transducing systems: hallmarks and uncertainties of CO, NO, and H2S gas biology. Antioxidants & redox signaling 13:157-192; 2010.

[10] Ubuka, T. Assay methods and biological roles of labile sulfur in animal tissues. J. Chromatogr. B Analyt. Techno. Biomed. Life Sci., 781:227-249; 2002.

[11] Ishigami, M.; Hiraki, K.; Umemura, K.; Ogasawara, Y.; Ishii, K.; Kimura, H. A source of hydrogen sulfide and a mechanism of its release in the brain. Antioxidants & redox signaling 11:205-214; 2009.

[12] Johnson, D. C.; Dean, D. R.; Smith, A. D.; Johnson, M. K. Structure, function, and formation of biological iron-sulfur clusters. Annual review of biochemistry 74:247-281; 2005.

[13] Levitt, M. D.; Abdel-Rehim, M. S.; Furne, J. Free and acid-labile hydrogen sulfide concentrations in mouse tissues: anomalously high free hydrogen sulfide in aortic tissue. Antioxidants & redox signaling 15:373-378; 2011.

[14] Wintner, E. A.; Deckwerth, T. L.; Langston, W.; Bengtsson, A.; Leviten, D.; Hill, P.; Insko, M. A.; Dumpit, R.; VandenEkart, E.; Toombs, C. F.; Szabo, C. A monobromobimane-based assay to measure the pharmacokinetic profile of reactive sulphide species in blood. British journal of pharmacology 160:941-957; 2010.

[15] Whiteman, M.; Le Trionnaire, S.; Chopra, M.; Fox, B.; Whatmore, J. Emerging role of hydrogen sulfide in health and disease: critical appraisal of biomarkers and pharmacological tools. Clin Sci (Loud) 121:459-488; 2011.

[16] Doeller, J. E.; Isbell, T. S.; Benavides, G.; Koenitzer, J.; Patel, H.; Patel, R. P.; Lancaster, J. R., Jr.; Darley-Usmar, V. M.; Kraus, D. W. Polarographic measurement of hydrogen sulfide production and consumption by mammalian tissues. Analytical biochemistry 341:40-51; 2005.

[17] Tangerman, A.; Meuwese-Arends, M. T.; van Tongeren, J. H. New methods for the release of volatile sulfur compounds from human serum: its determination by Tenax trapping and gas chromatography and its application in liver diseases. The Journal of laboratory and clinical medicine 106:175-182; 1985.

[18] Shen, X.; Pattillo, C. B.; Pardue, S.; Bir, S. C.; Wang, R.; Kevil, C. G. Measurement of plasma hydrogen sulfide in vivo and in vitro. Free radical biology & medicine 50:1021-1031; 2011.

[19] Olson, K. R. Is hydrogen sulfide a circulating "gasotransmitter" in vertebrate blood? Biochimica et biophysica acta 1787:856-863; 2009.

[20] Furne, J.; Saeed, A.; Levitt, M. D. Whole tissue hydrogen sulfide concentrations are orders of magnitude lower than presently accepted values. American journal of physiology 295:R1479-1485; 2008.

[21] Togawa, T.; Ogawa, M.; Nawata, M.; Ogasawara, Y.; Kawanabe, K.; Tanabe, S. High performance liquid chromatographic determination of bound sulfide and sulfite and thiosulfate at their low levels in human serum by pre-column fluorescence derivatization with monobromobimane. Chemical & pharmaceutical bulletin 40:3000-3004; 1992.

[22] Kosower, N. S.; Kosower, E. M. Thiol labeling with bromobimanes. Methods in enzymology 143:76-84; 1987.

[23] Tanabe, S. [Development of assay methods for endogenous inorganic sulfur compounds and sulfurtransferases and evaluation of the physiological functions of bound sulfur]. Yakugaku Zasshi 128:881-900; 2008.

[24] Han, J. C.; Han, G. Y. A procedure for quantitative determination of tris(2-carboxyethyl)phosphine, an odorless reducing agent more stable and effective than dithiothreitol. Analytical biochemistry 220:5-10; 1994.

[25] Graham, D. E.; Harich, K. C.; White, R. H. Reductive dehalogenation of monobromobimane by tris(2-carboxyethyl)phosphine. Analytical biochemistry 318:325-328; 2003.

[26] Tyagarajan, K.; Pretzer, E.; Wiktorowicz, J. E. Thiol-reactive dyes for fluorescence labeling of proteomic samples. Electrophoresis 24:2348-2358; 2003.

[27] Rao, G. S.; Gorin, G. Organic Chemistry 24:749-753; 1959.

[28] Cavallini, D.; De Marco, C.; Mondovi, B.; Mori, B. G. The cleavage of cystine by cystathionase and the transulfuration of hypotaurine. Enzymologia 22:161-173; 1960.

[29] Sorbo, B. On the formation of thiosulfate from inorganic sulfide by liver tissue and heme compounds. Biochimica et biophysica acta 27:324-329; 1958.

[30] Zal, F.; Leize, E.; Lallier, F. H.; Toulmond, A.; Van Dorsselaer, A.; Childress, J. J. S-Sulfohemoglobin and disulfide exchange: the mechanisms of sulfide binding by Riftia pachyptila hemoglobins. Proceedings of the National Academy of Sciences of the United States of America 95:8997-9002; 1998.

[31] Deleon, E. R.; Stoy, G. F.; Olson, K. R. Passive loss of hydrogen sulfide in biological experiments. Analytical biochemistry; 2011.

[32] Unger, J.; Filippi, G.; Patsch, W. Measurements of free hemoglobin and hemolysis index: EDTA- or lithium-heparinate plasma? Clinical chemistry 53:1717-1718; 2007.

[33] Peng, H.; Cheng, Y.; Dai, C.; King, A. L.; Predmore, B. L.; Lefer, D. J.; Wang, B. A fluorescent probe for fast and quantitative detection of hydrogen sulfide in blood. Angewandte Chemie (International ed 50:9672-9675; 2011.

[34] Qian, Y.; Karpus, J.; Kabil, O.; Zhang, S. Y.; Zhu, H. L.; Banerjee, R.; Zhao, J.; He, C. Selective fluorescent probes for live-cell monitoring of sulphide. Nature communications 2:495; 2011.

[35] Lippert, A. R.; New, E. J.; Chang, C. J. Reaction-based fluorescent probes for selective imaging of hydrogen sulfide in living cells. Journal of the American Chemical Society 133:10078-10080; 2011.

[36] Mubeen, S.; Zhang, T.; Chartuprayoon, N.; Rheem, Y.; Mulchandani, A.; Myung, N. V.; Deshusses, M. A. Sensitive detection of H2S using gold nanoparticle decorated single-walled carbon nanotubes. Analytical chemistry 82:250-257; 2010.

[37] Zhang, B. H.; Wu, F. Y.; Wu, Y. M.; Zhan, X. S. Fluorescent method for the determination of sulfide anion with ZnS:Mn quantum dots. Journal of fluorescence 20:243-250; 2010.

[38] Zhang, X; Kraus, D. Sensor for measurement of hydrogen sulfide. US 2012/0073988 A1; 2012.

[39] Kolluru, G. K., Shen, X., Kevil, C. K. Detection of hydrogen sulfide in biological samples: current and future, Expert Reviews, 4: 9-12; 2011.

[40] Olson, K. H. A practical look at the chemistry and biology of hydrogen sulfide. Antioxidants & Redox Signaling, 17: 32-44; 2012.

[41] O'Reilly, J. W.; Dicinoski, G. W.; Shaw, M. J.; Haddad, P. R. Chromatographic and electrophoretic separation of inorganic sulfur and sulfur-oxygen species. Analytica Chimica Acta, 432:165-192; 2001.

[42] Burns, J. A.; Butler, J. C.; Moran, J.; Whitesides, G. M. Selective reduction of disulfides by tris(2-carboxyethyl) phosphine. J. Org. Chem. 56:2648-2650.

The complete disclosures of all references cited in this specification are hereby incorporated by reference. Specifically incorporated by reference is the following reference: X. Shen et al., Analytical measurement of discrete hydrogen sulfide pools in biological specimens, Free Radical Biology and Medicine, vol. 52, 2276-2283 (2012), published online 19 Apr. 2012. In the event of an otherwise irreconcilable conflict, however, the present specification shall control.

What is claimed:

1. A method to measure in a sample the concentrations of free $H_2S$, of acid-labile sulfide, and of sulfane-bound sulfur; said method comprising the following steps:
   (a) placing separate portions X, Y, and Z of the sample into three individual evacuated containers, whereby most of the free $H_2S$ will partition into the headspaces of each of the respective containers;
   (b) combining portion X with an alkaline buffer, a chelating agent to chelate any trace metals that may be present in the sample, and monobromobimane, and incubating under low oxygen conditions; whereby free $H_2S$ will react with the monobromobimane to form a sulfide-dibimane product; chromatographically separating the sulfide-dibimane product from other components of the resulting mixture; and fluorimetrically measuring the amount of the separated sulfide-dibimane product as a measure of the concentration of free $H_2S$ in the sample (Result B);
   (c) combining portion Y with an acid buffer and incubating to release acid-labile sulfide as free $H_2S$, the portion Y including a liquid segment and a gaseous segment; removing the liquid segment of portion Y; combining the gaseous segment of portion Y with an alkaline buffer, a chelating agent to chelate any trace metals that may be present in the sample, and monobromobimane, and incubating under low oxygen conditions; whereby free $H_2S$ will react with the monobromobimane to form a sulfide-dibimane product; chromatographically separating the sulfide-dibimane product from other components of the resulting mixture; and fluorimetrically measuring the amount of the separated sulfide-dibimane product as a measure of the combined concentration of acid-labile sulfide and free $H_2S$ in the sample (Result A);
   (d) combining portion Z with an acid buffer and a reducing agent to release both acid-labile sulfide and sulfane sulfur as free $H_2S$, the portion Z including a liquid segment and a gaseous segment; removing the liquid segment of portion Z; combining the gaseous segment of portion Z with an alkaline buffer, a chelating agent to chelate any trace metals that may be present in the sample, and monobromobimane, and incubating under low oxygen conditions; whereby free $H_2S$ will react with the monobromobimane to form a sulfide-dibimane product; chromatographically separating the sulfide-dibimane product from other components of the resulting mixture; and fluorimetrically measuring the amount of the separated sulfide-dibimane product as a measure of the combined concentration of sulfane sulfur, acid-labile sulfide, and free $H_2S$ in the sample (Result C); and
   (e) determining the concentration of free $H_2S$ in the sample as equal to Result B; determining the concentration of acid-labile sulfide in the sample as equal to the difference between Result A and Result B; and determining the amount of sulfane sulfur as equal to the difference between Result C and Result A.

2. The method of claim 1, wherein the reducing agent is tris(2-carboxyethyl)phosphine hydrochloride.

3. The method of claim 1, wherein the alkaline buffer in steps (b)-(d) has a pH between about 8.0 and 10.0.

4. The method of claim 1, wherein the alkaline buffer in steps (b)-(d) has a pH about 9.5.

5. The method of claim 1, wherein the oxygen concentration in steps (b)-(d) is less than about 5%.

6. The method of claim 1, wherein the oxygen concentration in steps (b)-(d) is less than or equal to about 1%.

7. The method of claim 1, wherein the chelating agent in steps (b)-(d) is diethylenetriaminepentaacetic acid.

8. The method of claim 1, wherein the sulfide-dibimane in steps (b)-(d) is stabilized by adding sulfosalicylic acid.

9. The method of claim 1, wherein the acid buffer in steps (c)-(d) has a pH less than about 4.0.

10. The method of claim 1, wherein the acid buffer in steps (c)-(d) has a pH between about 2.0 and about 3.0.

11. The method of claim 1, wherein the acid buffer in steps (c)-(d) has a pH about 2.6.

12. The method of claim 1, wherein the molar ratio of the reducing agent to monobromobimane in step (d) is about 1:10.

13. The method of claim 1, wherein the time of incubation in each of steps (b)-(d) is about 30 minutes.

14. The method of claim 1, wherein the sample is selected from the group consisting of plasma, blood, tissue, spinal fluid, urine, other body fluids, cells, and environmental water.

15. The method of claim 1, wherein the sample is plasma.

16. A method to measure concentrations of free $H_2S$, acid-labile sulfide, and sulfane-bound sulfur in a sample comprising:
   placing first, second, and third separate portions of the sample into a respective first, second, and third evacuated containers,
   adding an alkaline buffer, a chelating agent, and monobromobimane to the first portion, and incubating under low oxygen condition;
   separating a sulfide-dibimane product from the first portion; and
   measuring an amount of the sulfide-dibimane product separated from the first portion as a measure of the concentration of free $H_2S$ in the sample;
   adding an acid buffer to the second portion and incubating to release acid-labile sulfide as free $H_2S$, the second portion including a liquid segment and a gaseous segment;
   removing the liquid segment of the second portion;
   combining the gaseous segment of the second portion with an alkaline buffer, a chelating agent, and monobromobimane, and incubating under low oxygen conditions;
   separating a sulfide-dibimane product from the second portion;
   measuring an amount of the sulfide-dibimane product separated from the second portion as a measure of a combined concentration of acid-labile sulfide and free $H_2S$ in the sample;
   adding an acid buffer and a reducing agent to the third portion, the third portion including a liquid segment and a gaseous segment;
   removing the liquid segment of the third portion;
   combining the gaseous segment of the third portion with an alkaline buffer, a chelating agent, and monobromobimane,
   incubating the third portion under low oxygen conditions;
   separating a sulfide-dibimane product from the third portion;
   measuring an amount of the sulfide-dibimane product separated from the third portion as a measure of the combined concentration of sulfane sulfur, acid-labile sulfide, and free $H_2S$ in the sample; and one of
- determining the concentration of free $H_2S$ in the sample as equal to the measure of the concentration of free $H_2S$ in the sample;
- determining the concentration of acid-labile sulfide in the sample as equal to a difference between the measure of the combined concentration of acid-labile sulfide and free $H_2S$ in the sample and the measure of the concentration of free $H_2S$ in the sample; and
- determining the concentration of sulfane sulfur in the sample as equal to a difference between the measure of the combined concentration of sulfane sulfur, acid-labile sulfide, and free $H_2S$ in the sample and the measure of the combined concentration of acid-labile sulfide and free $H_2S$ in the sample.

17. A method to measure concentrations of one of acid-labile sulfide and sulfane-bound sulfur in a sample comprising:

one of
(1) placing a first and a second separate portions of the sample into a respective first and second evacuated containers;
- adding an alkaline buffer, a chelating agent, and monobromobimane to the first portion, and incubating under low oxygen condition;
- separating a sulfide-dibimane product from the first portion; and
- measuring an amount of the sulfide-dibimane separated from the first portion;
- adding an acid buffer to the second portion and incubating to release acid-labile sulfide as free $H_2S$, the second portion including a liquid segment and a gaseous segment;
- removing the liquid segment of the second portion;
- combining the gaseous segment of the second portion with an alkaline buffer, a chelating agent, and monobromobimane, and incubating under low oxygen conditions;
- separating a sulfide-dibimane product from the second portion;
- measuring an amount of the sulfide-dibimane product separated from the second portion; and
- determining a measurement of the concentration of acid-labile sulfide in the sample as equal to a difference between the amount of sulfide-dibimane product separated from the first portion and the amount of the sulfide-dibimane product separated from the second portion; and (2) placing a second and a third separate portions of the sample into a respective second and third evacuated containers; and
- adding an acid buffer to the second portion and incubating to release acid-labile sulfide as free $H_2S$, the second portion including a liquid segment and a gaseous segment;
- removing the liquid segment of the second portion;
- combining the gaseous segment of the second portion with an alkaline buffer, a chelating agent, and monobromobimane, and incubating under low oxygen conditions;
- separating a sulfide-dibimane product from the second portion;
- measuring an amount of the sulfide-dibimane product separated from the second portion;
- adding an acid buffer and a reducing agent to the third portion, the third portion including a liquid segment and a gaseous segment;
- removing the liquid segment of the third portion;
- combining the gaseous segment of the third portion with an alkaline buffer, a chelating agent, and monobromobimane,
- incubating the third portion under low oxygen conditions;
- separating a sulfide-dibimane product from the third portion;
- measuring an amount of the sulfide-dibimane product separated from the third portion; and
- determining a measurement of the concentration of sulfane sulfur in the sample as equal to a difference between the amount of the sulfide-dibimane product separated from the second portion and the amount of the sulfide-dibimane product separated from the third portion.

18. The method of claim 17 wherein the amount of acid-labile sulfide is measured.

19. The method of claim 17 wherein the amount of sulfane sulfur is measured.

* * * * *